United States Patent
Booth

(10) Patent No.: US 8,156,439 B2
(45) Date of Patent: Apr. 10, 2012

(54) METHOD AND APPARATUS FOR MIMICKING THE DISPLAY LAYOUT WHEN INTERFACING TO MULTIPLE DATA MONITORS

(75) Inventor: John Booth, Tampa, FL (US)

(73) Assignee: The General Electric Company, Schenectady, NY (US)

( * ) Notice: Subject to any disclaimer, the term of this patent is extended or adjusted under 35 U.S.C. 154(b) by 707 days.

(21) Appl. No.: 11/739,211

(22) Filed: Apr. 24, 2007

(65) Prior Publication Data

US 2008/0270912 A1    Oct. 30, 2008

(51) Int. Cl.
*G06F 3/00* (2006.01)
(52) U.S. Cl. .................. 715/748; 715/744; 709/231
(58) Field of Classification Search .......... 715/748, 715/744; 709/231, 232, 236
See application file for complete search history.

(56) References Cited

U.S. PATENT DOCUMENTS

| | | | | |
|---|---|---|---|---|
| 5,819,741 | A * | 10/1998 | Karlsson et al. | 600/523 |
| 6,205,235 | B1 * | 3/2001 | Roberts | 382/128 |
| 6,224,549 | B1 * | 5/2001 | Drongelen | 600/300 |
| 6,475,146 | B1 * | 11/2002 | Frelburger et al. | 600/437 |
| 6,957,102 | B2 * | 10/2005 | Silver et al. | 607/2 |
| 7,134,994 | B2 * | 11/2006 | Alpert et al. | 600/300 |
| 7,305,691 | B2 * | 12/2007 | Cristofalo | 725/34 |
| 2002/0198473 | A1 * | 12/2002 | Kumar et al. | 600/595 |
| 2004/0102687 | A1 * | 5/2004 | Brashears et al. | 600/323 |
| 2004/0186357 | A1 * | 9/2004 | Soderberg et al. | 600/300 |
| 2004/0243448 | A1 * | 12/2004 | Shoji et al. | 705/3 |
| 2005/0204310 | A1 * | 9/2005 | De Zwart et al. | 715/821 |
| 2005/0222499 | A1 * | 10/2005 | Banik et al. | 600/132 |
| 2005/0288571 | A1 * | 12/2005 | Perkins et al. | 600/407 |
| 2006/0094936 | A1 * | 5/2006 | Russ | 600/300 |
| 2006/0149597 | A1 * | 7/2006 | Powell et al. | 705/2 |
| 2006/0155589 | A1 * | 7/2006 | Lane et al. | 705/4 |
| 2006/0161054 | A1 * | 7/2006 | Reuss et al. | 600/300 |
| 2006/0173951 | A1 * | 8/2006 | Arteaga et al. | 709/203 |
| 2006/0238333 | A1 * | 10/2006 | Welch et al. | 340/539.12 |
| 2006/0276714 | A1 * | 12/2006 | Holt et al. | 600/481 |
| 2007/0103725 | A1 * | 5/2007 | Kawahara et al. | 358/1.15 |
| 2007/0254593 | A1 * | 11/2007 | Jollota et al. | 455/67.11 |
| 2007/0258395 | A1 * | 11/2007 | Jollota et al. | 370/310 |

(Continued)

OTHER PUBLICATIONS

EKO Systems, Inc. (2005) "Charting Station Keyboard" website: www.ekosystems.com/frontiersKeyboard.php; date accessed: Feb. 8, 2007.

*Primary Examiner* — Ba Huynh
(74) *Attorney, Agent, or Firm* — Andrus, Sceales, Starke & Sawall, LLP

(57) ABSTRACT

A computer for use in the transfer and monitoring of data and a method of verifying the transfer of patient physiological data is herein disclosed. The computer comprises a display for displaying data, a controller for controlling the display of the data, a graphical user interface being disposed to display data, a first input device connected to the controller for entering data that is recorded and displayed by a data recording device and a second input device connected to the controller for entering data into the controller that is indicative of the spatial arrangement of the display of the data by the data recording device, wherein the controller uses the data indicative of the spatial arrangement of the display of data by the data recording device to display the data in the graphical user interface according to the data by the data recording device.

19 Claims, 5 Drawing Sheets

U.S. PATENT DOCUMENTS

| | | | |
|---|---|---|---|
| 2007/0282208 A1* | 12/2007 | Jacobs et al. | 600/485 |
| 2008/0003555 A1* | 1/2008 | Ekvall et al. | 434/262 |
| 2008/0004904 A1* | 1/2008 | Tran | 705/2 |
| 2008/0097175 A1* | 4/2008 | Boyce et al. | 600/323 |
| 2008/0176543 A1* | 7/2008 | Gravel et al. | 455/414.2 |
| 2008/0194918 A1* | 8/2008 | Kulik et al. | 600/300 |
| 2009/0054735 A1* | 2/2009 | Higgins et al. | 600/300 |
| 2009/0066713 A1* | 3/2009 | Ando | 345/581 |
| 2009/0221880 A1* | 9/2009 | Soderberg et al. | 600/300 |
| 2010/0056883 A1* | 3/2010 | Meschisen et al. | 600/301 |
| 2010/0172680 A1* | 7/2010 | Butcher | 400/76 |

* cited by examiner

METHOD AND APPARATUS FOR MIMICKING THE DISPLAY LAYOUT WHEN INTERFACING TO MULTIPLE DATA MONITORS

FIELD OF THE DISCLOSURE

The present disclosure relates to the field of data recording and verification. More specifically, the present disclosure relates to a method and apparatus in which the display of data on a computer display is modified to conform to the display of data by a data recording device.

BACKGROUND

The management of patient data within a hospital's information network has become of critical importance to the provision of care to the patients as well as to the operation of the hospital itself. In a typical hospital setting, a patient may be attached to one or more patient monitors or monitoring devices by a variety of electrodes and/or sensors. These patient monitors collect a variety of data from the patient, including a variety of patient physiological parameters. The monitored patient data is typically then electronically sent through the hospital's information network to a central database comprising the patient's electronic medical history records; alternatively, a clinician must periodically read the physiological data and physically record the data for entry into the electronic patient medical history records.

Many patient monitoring devices are expensive, such that most hospitals do not have patient monitoring devices in a one-to-one ratio with the patients. Therefore, these monitoring devices may be mobile in nature, such as being located on a wheeled cart, so that a clinician may periodically transport the monitoring device to each patient to use in collecting and recording the patient physiological data. The monitoring device may connect to the hospital's network and transmit the physiological data to the patient's electronic medical record (EMR) or electronic health record (EHR) at the request of the clinician. Alternatively, if the monitoring device is not connected to the hospital's network, the clinician may use a computer that is connected to the hospital's network to record the data that is collected and displayed by the monitoring device into the patient's EMR.

However, the electronic recordation of the patient's physiological data in the patient's electronic medical record is not advantageous unless the data recorded is correct. Therefore, it is imperative for the clinician to properly enter the physiological data and to check that the data recorded in the EMR coincides with the data collected and displayed by the monitoring device. Currently, a hospital may use a variety of different models of monitoring devices from a common manufacturer, and/or monitoring devices from a plurality of different manufacturers. Each monitoring device may differ slightly in operation and the display of data. As a result, the clinician must learn the displays of physiological data on each of the monitoring devices. As the clinician moves from device to device during the course of a shift, the clinician may become confused when recording data or verifying that the data in the EMR matches the data displayed by the monitoring device. This leads to unidentified errors in the recorded patient physiological data. These errors may in turn lead to later diagnostic errors. Additionally, in situations wherein the clinician must use a computer to enter the physiological data that is displayed by the monitoring device, the different spatial orientations of the data on the different monitoring devices may cause confusion by the clinician, leading to the entry of physiological data into the improper data fields of the computer. This improper entry of data may include the transposition of physiological parameters, resulting in the recordation of improper physiological data values in the EMR.

Therefore, it is desirable for a device that assists the clinician in verifying that the proper physiological data has been recorded in the electronic patient medical history record.

SUMMARY OF THE DISCLOSURE

The present disclosure includes a computer for use in the transfer and verification of data that comprises a display for displaying data, a controller connected to the display, and a graphical user interface displayed on the display. The controller controls the display of data on the display and the graphical user interface is disposed to display data. A first input device is connected to the controller and is used to enter data into the controller that has been recorded and displayed by a data recording device. The controller causes the data to be displayed in the graphical user interface on the display. A second input device is connected to the controller such that data is entered into the controller that is indicative of the spatial arrangement of the display of data by the data recording device. The controller uses the data indicative of the spatial arrangement of the display of the data by the data recording device to display the data in a graphical user interface according to the same spatial arrangement as the display of the data by the data recording device.

In an embodiment of the apparatus herein disclosed, the controller controls the display of data in the graphical user interface such as to mimic the appearance of the display of data by the data recording device.

In a further embodiment of the apparatus herein disclosed, the data recording device is a patient physiological data monitor and the data that is recorded and displayed by the data recording device is patient physiological data.

In a still further embodiment of the apparatus herein disclosed, the data recording device is a vital signs monitor, and the patient physiological data includes patient temperature, patient SpO$_2$, and patient blood pressure.

The disclosure is also directed to a method of verifying the transfer of patient physiological data recorded by a patient monitor to a computer. The method of verifying the transfer of patient physiological data comprises receiving patient physiological data acquired by the patient monitor, receiving a signal indicative of the spatial format of the display of the physiological data on the patient monitor, displaying the physiological data on the computer in the same spatial format as the display of the physiological data on the patient monitor, and verifying that the physiological data displayed on the patient monitor matches the physiological data displayed on the computer.

DETAILED DISCLOSURE

Figure 1:
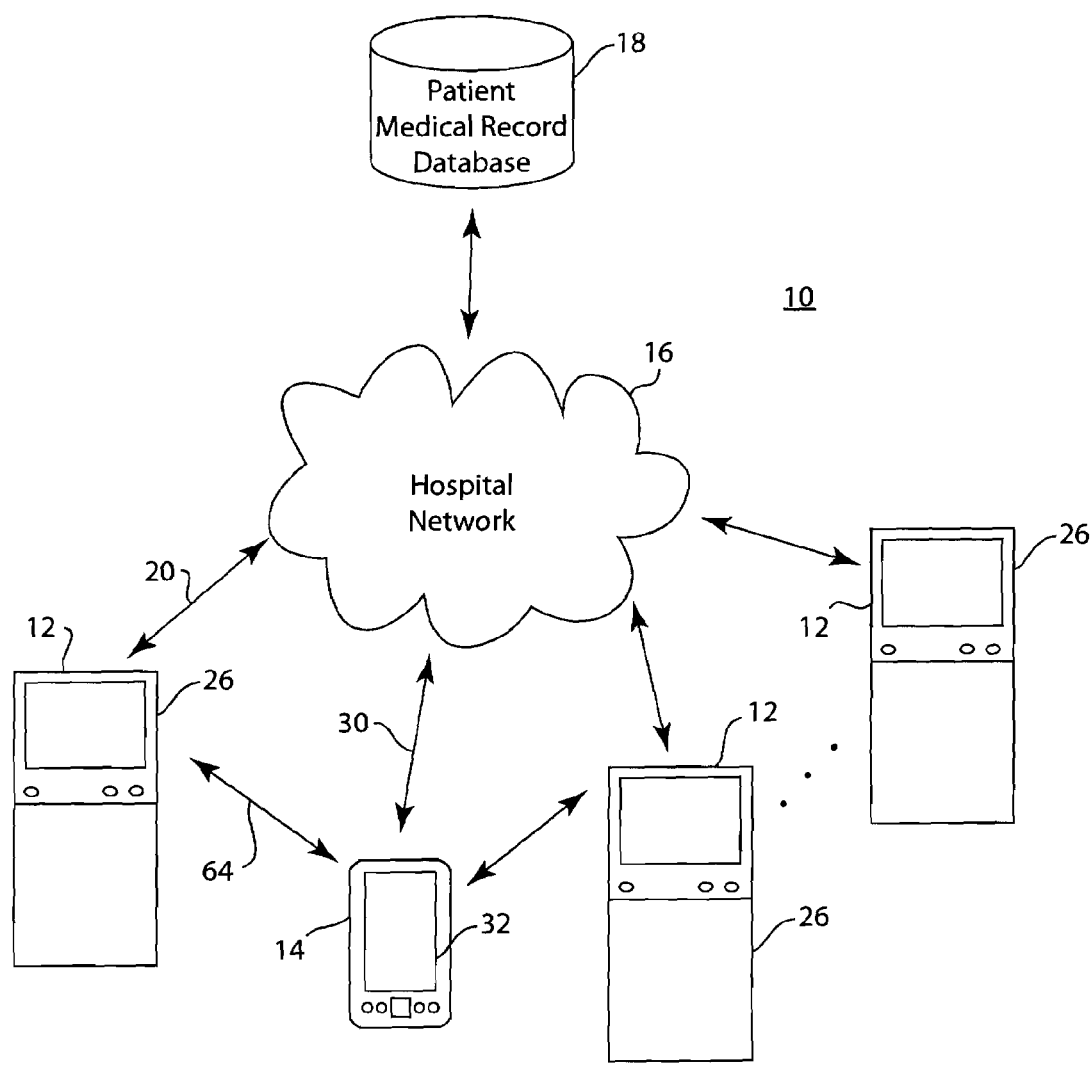
FIG. 1 is a schematic diagram of a hospital information system.

FIG. 1 depicts a hospital information system 10 that includes a plurality of data recording devices 12, which in the embodiment herein depicted as patient physiological data monitors 12. It is understood that although the present disclosure focuses on an embodiment utilizing patient monitors, any application wherein a data recording device collects and displays data that must be collected and/or verified by an observer may utilize the device and method disclosed herein. The patient monitor 12 may record a variety of patient physiological parameters that may be received from a variety of electrodes and/or sensors attached to a patient. In a further embodiment, the patient monitor 12 may be a vital signs monitor (VSM) that monitors the physiological parameters of: body temperature, SpO$_2$, and blood pressure. Additional parameters that may be monitored by the patient monitor 12 may include, but are not limited to, mean arterial pressure (MAP), patient heart rate measured in beats per minute (BPM), patient respiration rate, and patient pain indicia.

The information system 10 further comprises a computer 14 that is connected to a hospital network 16. The computer 14 may comprise a handheld computer such as a PDA, or other portable type computer such as a laptop, or any other similar type of computer. Furthermore, the computer 14 may comprise a desktop computer that is kept at a fixed location, such as in each individual patient's room in the hospital. The computer 14 is connected to a hospital network 16 which may comprise a local area network (LAN) comprising wired and/or wireless communication within a hospital. The hospital network 16 may further comprise a wide-area network (WAN) that connects multiple buildings and/or hospital locations in a single hospital information network. Such a network may also utilize the internet to facilitate the transfer of data.

The patient monitor 12 may be connected to the hospital network 16, and/or may be connected directly to the computer 14 such as to facilitate data transfer between these three locations. However, in alternative embodiments of the information system 10, the patient monitor 12 does not comprise a data connection to the hospital network 16 and/or the computer 14.

The hospital network 16 is further connected to the patient medical record database 18. The electronic medical record (EMR) or electronic health record (EHR) for each patient in the hospital may be stored in the patient medical record database 18. Any physiological data recorded from the patient may be recorded in either the EMR or the EHR. For the present disclosure, it will be assumed that data is recorded in the patient's EMR; however, it is understood that any type of patient electronic record, including, but not limited to the patient's EHR may be used. Therefore, it is necessary that the data received by the patient monitor 12 be transmitted to the patient medical record database 18 and stored therein. The data connection to the patient medical record database 18 is facilitated by the hospital network 16 which connects the patient monitor 12 and/or the computer 14 to the patient medical records database 18.

Figure 2:
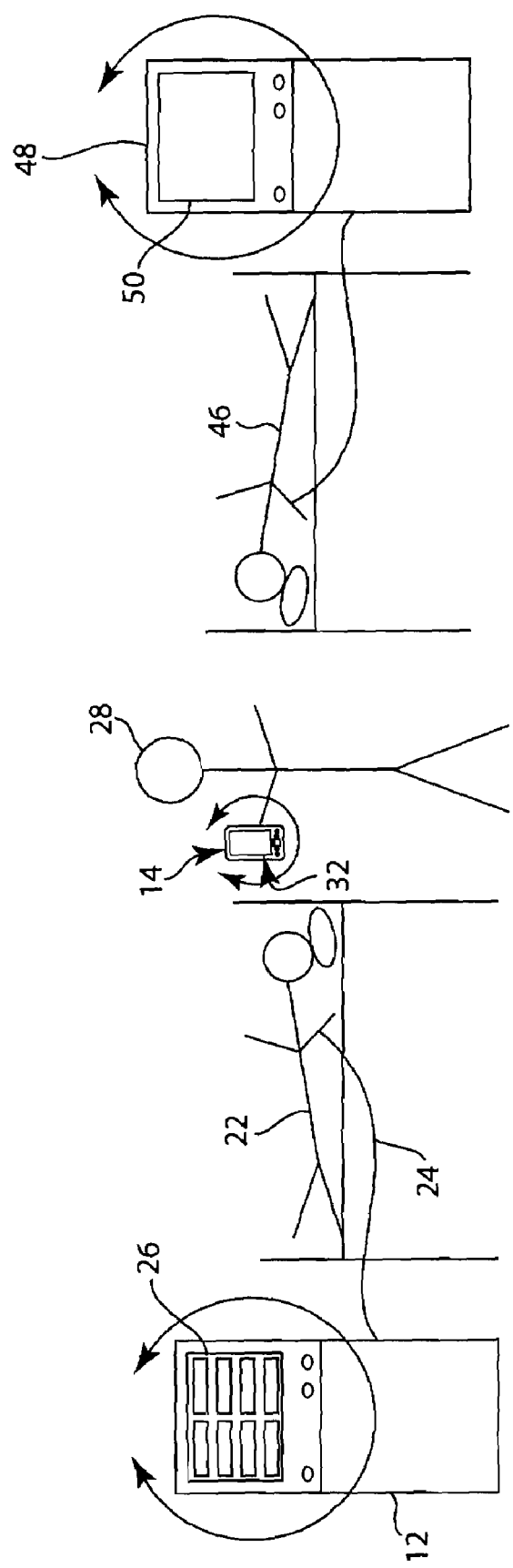
FIG. 2 depicts an interaction between a clinician and a monitoring device.

FIG. 2 illustrates an embodiment in which the patient monitor 12 is connected to a patient 22 by one or more leads 24 to collect and monitor physiological data from the patient 22. The patient physiological data is displayed on a display 26 of the patient monitor 12. The patient monitor 12 also comprises the capability to transfer the collected patient physiological data via data connection 20 through the hospital network 16 to the patient medical record database 18, as shown in FIG. 1. Referring back to FIG. 2, when the clinician 28 enters the room wherein the patient monitor 12 and the patient 22 are located, the clinician 28 may verify that the transfer of the patient physiological data from the patient monitor 12 to the patient medical record database 18 has been successfully performed. The clinician 28 uses a computer 14 which may be a PDA, laptop, or desktop computer to access the patient medical record database 18 via a data connection 30 and the hospital network 16, as shown in FIG. 1. The computer 14 may further comprise a display 32 to display the patient physiological data from the patient medical record database 18.

Figure 3A:
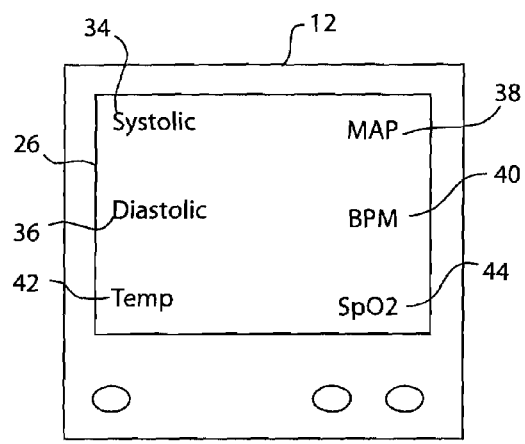
FIG. 3a depicts an embodiment of a display of a data recording device.
Figure 3B:
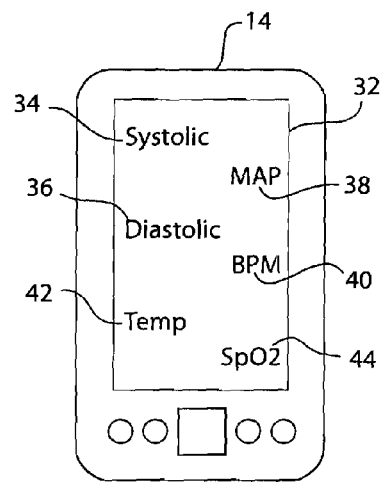
FIG. 3b depicts an embodiment of a computer.

As can be understood in FIG. 2, the clinician 28 can verify the accuracy of the data transfer between the patient monitor 12 and the patient medical record database 18 by comparing the values for the patient physiological data that are displayed on the display 32 of the computer 14 with the physiological data values that are displayed on the display 26 of the patient monitor 12. To facilitate this review, the computer 14 modifies the display of physiological data on the display 32 such that the spatial relationship between the individual physiological parameters displayed on the display 32 matches the spatial relationship of the display of physiological parameters on display 26. An example of the displays 26 and 32 are depicted in FIGS. 3a and 3b. In the embodiment depicted in FIGS. 3a and 3b, the display of physiological parameters may comprise systolic 34 and diastolic 36 blood pressures, the mean arterial pressure (MAP) 38, the breaths per minute (BPM) 40, the temperature 42 and the SpO$_2$ 44; however, this in no way limits the types of data that may displayed on the displays 26 and 32.

The fact that the display of the physiological data on display 32 matches the display of the physiological data on display 26 facilitates the clinician's ability to quickly and visually check the values for the physiological parameters to ensure that the physiological data recorded by the patient monitor 12 matches the physiological data that has been recorded in the patient medical records database as shown on the computer 14.

Figure 4A:
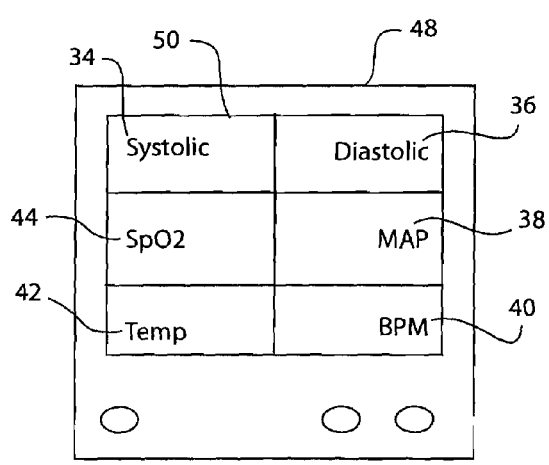
FIG. 4a depicts a second embodiment of a data recording device.

Referring back to FIG. 2, when the clinician 28 finishes with the patient 22, the clinician moves to the next patient 46, who may be in a location remote from the patient 22 and the patient monitor 12. Therefore, a different patient monitor 48 may be used to collect physiological data from the patient 46. The patient monitor 48 may be of a different model or different brand than that of patient monitor 12. A result of these differences may be that the display of data on the patient monitor 48, as depicted in FIG. 4a, may differ from the display of physiological data on the patient monitor 12, as depicted in FIG. 3a. A comparison of the spatial arrangements of the physiological parameters of systolic pressure 34, diastolic pressure 36, MAP 38, BPM 40, temperature 42, and SpO$_2$ 44 on the display 50 of the patient monitor 48 in FIG. 4a as opposed to the display 26 of the patient monitor 12 in FIG. 3a illustrates one embodiment of these such differences. The computer 14 modifies the spatial relationship of the display of physiological parameters on the display 32 (FIG. 4b) to match the spatial relationship of the physiological parameters as displayed on display 50. Therefore, the clinician 28 is aided in the clinician's job of verifying the physiological data recorded with the physiological data that is displayed on each of the displays 26 and 50, respectively.

Figure 4B:
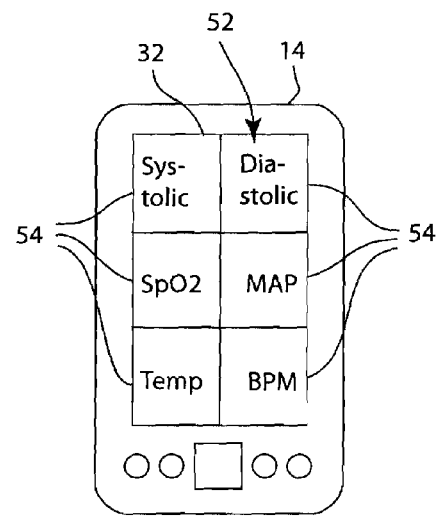
FIG. 4b depicts a second embodiment of a computer.

FIG. 4b depicts an embodiment of the display 32 of the computer 14 wherein the display 32 further comprises a graphical user interface 52 for the display of the physiological data. The graphical user interface 52 may further comprise a plurality of data regions 54, with each data region being disposed to display a particular physiological parameter. In this embodiment, the computer 14 matches the spatial relationship of the display of the physiological data on the display 50 of the patient monitor 48 by rearranging the data regions 54 within the graphical user interface 52.

In an alternative embodiment, the patient monitor 12 may not be connected to the hospital network 16 via the data connection 20. This is not an uncommon situation as the patient monitor 12 is often a portable unit that must be moved to and from a number of patient's rooms by the clinician during the course of the day. The constant movement of the patient monitor 12 may present a barrier to the patient monitor 12 being connected to the network 16. Therefore, in this embodiment, the computer 14 further acts as the data transfer device that facilitates the transfer of the physiological data from the patient monitor 12 to the patient medical record database 18. The clinician 28 must view the display of physiological data on the display 26 of the patient monitor 12 and enter the physiological data values into the computer 14. The computer 14 facilitates the entry of these physiological data values, and promotes the accurate entry of the physiological data into the proper data fields by conforming the spatial relationship of the data regions 54 with the display of the physiological data on the display 26 of the patient monitor 12. Therefore, the computer 14 aides the clinician in the proper recordation of the physiological data in the proper data fields such that the physiological data may be correct transmitted via the data connection 30 and the hospital network 16 to the patient medical record database 18.

Figure 5:
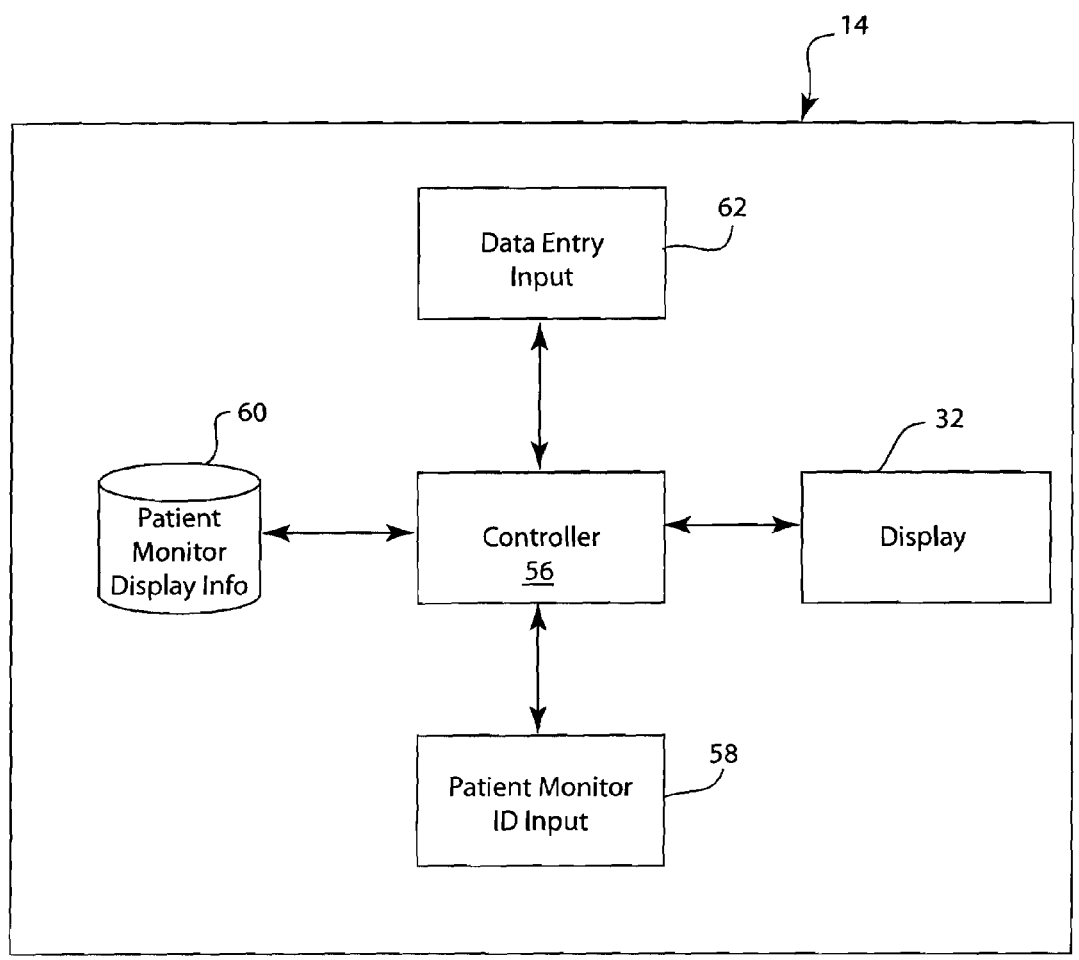
FIG. 5 is a schematic diagram of an embodiment of a computer.

The functionality herein described requires that the computer 14 be provided with an indication of the type and model of the patient monitor 12, 48 that the clinician 28 is checking such that the proper spatial relationship for the physiological data is displayed on the display 32 of the computer 14. FIG. 5 depicts a schematic diagram of the components within the computer 14 such as to effectuate this display. The computer 14 comprises a controller 56 that controls the display 32. The controller 56 may comprise any sort of processor, microprocessor, server, or other controller known in the art.

Before the controller 56 of the computer 14 can modify the display 32 of the physiological parameters, the controller 56 must receive an identification of the patient monitor 12 that the clinician 28 will be viewing. A patient monitor I.D. input 58 receives an indication of the patient monitor 12 that the clinician will be reviewing. The patient monitor I.D. input 58 may comprise a wide variety of input devices. These input devices may comprise input devices that automatically identify the patient monitor 12, such as an RFID sensor integrated in the computer 14 such that the RFID sensor may identify the patient monitor 12 by an RFID tag that is attached to or associated with and identifying the patient monitor 12. Alternatively, other automatic input devices may comprise a wireless or wired connection between the computer 14 and the patient monitor 12 such that the controller 56 may send a signal to the patient monitor 12 requiring the patient monitor 12 to identify itself to the controller 56. Other forms of patient monitor I.D. inputs 58 may comprise those inputs that are manually entered by the clinician 28. Examples of manual patient monitor I.D. inputs 58 may include the use of a keyboard, stylist, mouse, track pad or touch screen to manually enter an identification number or other information from the patient monitor 12 into the controller 56. Alternatively, one of the aforementioned input devices may be used to selected the proper identification of the patient monitor 12 from a list of possible patient monitors. Other types of manual patient monitor I.D. inputs 58 may include an infrared transmitter or a bar code scanner whereby the clinician 28 may scan an indication of the identification of the patient monitor 12 which is then sent to the controller 56.

Once the controller 56 has received an identification of the patient monitor 12 from the patient monitor I.D. input 58, the controller controls the display 32 to conform to the spatial relationships of the physiological data displayed on the display 32. The controller 56 may acquire information regarding the spatial relationships of the data display from a database of patient monitor display information 60. The patient monitor display information database 60 may be stored in the computer 14, or alternatively, may be located remote from the computer 14, but accessible to the computer 14 through the data connection 30 and the hospital network 16. The controller 56 uses the patient monitor identification information received from the patient monitor I.D. input 58 to acquire data that indicates the proper spatial relationship of the display of physiological parameters by the patient monitor 12 from the patient monitor display information database 60.

After controller 56 has received an indication of the spatial relationships of the physiological data to be displayed, the controller 56 needs the physiological data to be displayed. A data entry input 62 receives the physiological data that is to be displayed by the controller 56 on the display 32. In the embodiment wherein the patient monitor 12 is connected to the hospital network 16 via the data connection 20, the patient monitor is able to record the physiological data in the patient medical records database 18. In this embodiment, the data entry input 62 may comprise the data connection 30. The data connection 30 facilitates the transfer of the patient physiological data from the patient medical record database 18 to the computer 14. The controller 56 then takes the physiological data received by the data entry input 62 and displays the physiological data on the display 32 based upon the spatial relationships of the physiological data as defined in the patient monitor display information database 60 using the patient monitor I.D. acquired by the patient monitor I.D. input 58.

The clinician 28 may use the coinciding display of data on the display 32 and the display 26 to verify that the physiological parameters recorded by the patient monitor 12 and displayed on display 26 are the same as the physiological parameters that have been stored in the patient medical record database 18 for that patient. This verification is facilitated as the same physiological data appears at the same location and spatial orientation on both the display 26 and the display 32.

In an alternative embodiment wherein the patient monitor 12 is not connected to the hospital network 16 by a data connection 20, the computer 14 must be used to input the physiological data into the patient medical record database 18. In this embodiment, the data entry input 62 may comprise automatic and/or manual data entry input 62 devices. As shown in FIG. 1, the automatic data entry input devices 62 may comprise a wired or wireless data connection 64 between the patient monitor 12 and the computer 14. The patient monitor 12 may then transmit the patient physiological data to the computer 14 via the data connection 64. The controller 56 then displays the physiological data on the display 32 in accordance with the spatial relationships defined in the patient monitor display database 60. Upon verification that the physiological data is correct, the clinician 28 may cause the physiological data to be saved in the patient's EMR on the patient medical record database 18.

In embodiments wherein the data entry input 62 is a manual input, the data entry input 62 may comprise an input such as a keyboard or a stylus associated with the computer 14. The manual data entry input 62 may require the controller 56 to control the display 32 to display data entry fields for each of the physiological parameters as opposed to values for each of the physiological parameters. Each of the physiological parameter values may then be entered into the proper data entry field. The controller 56 controls the display 32 to have the physiological parameter data fields coincide with the same spatial relationships of the physiological parameters displayed on the display 26 such that the clinician 28 may more easily record the values for the physiological parameters in the proper data field for that particular physiological parameter. Once the physiological parameter values have been entered into the data fields, the coinciding displays facilitate the clinician's verification that the data entered is correct. After the data has been verified, the clinician 28 can cause the physiological data to be saved in the patient's EMR on the patient medical record base 18.

In an alternative embodiment, the patient monitor 12 transmits the physiological data to the computer 14. The patient monitor 12 may embed a spatial arranged signal in the physiological data signal. The spatial arrangement signal may include coordinate data representative of the spatial location of the display of the physiological data by the display 26. The computer 14 may use this coordinate data to arrange the display of the physiological data by the display 32. In embodiments the spatial arrangement signal need not be embedded in the physiological data signal, but may be rather sent as an independent signal or data value in conjunction with the transmission of the physiological data.

Figure 6:
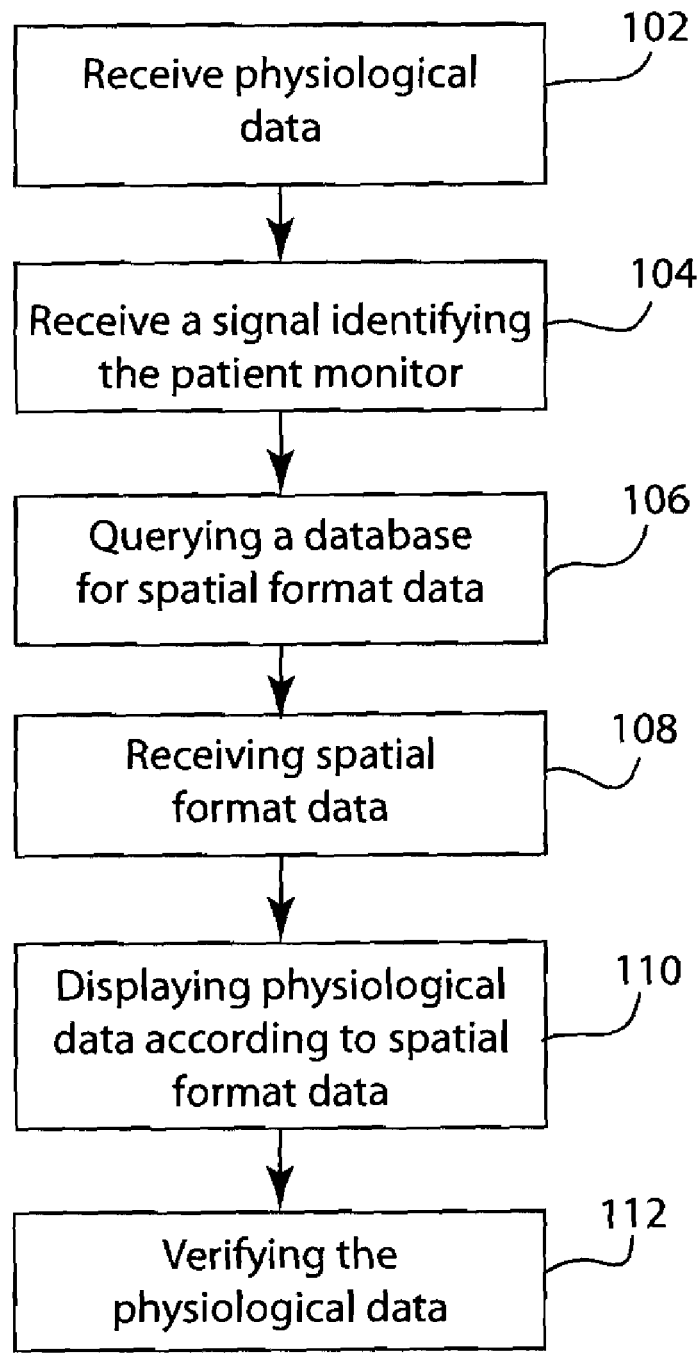
FIG. 6 is a flow chart depicting an embodiment of the method for verifying the transfer of data.

FIG. 6 depicts a flow chart of a method 100 of verifying the transfer of patient physiological data recorded by a patient monitor. The method 100 comprises the step of receiving physiological data 102 that has been acquired by the patient monitor. The patient physiological data may be received by a variety of sources including a wired or a wireless data connection, or by a form of manual input including a keypad or a stylus; however, the physiological data may be received in many other ways as well. Next, at step 104, a signal may be received, the signal being indicative of the patient monitor that acquired the patient physiological data. Similarly, the signal identifying the patient monitor may be received via a wired or wireless connection, or may be received by a manual input, such as a bar code scanner or RFID sensor; however, may other ways of receiving a signal identifying the patient monitor may be considered within the scope of 104.

Next, at step 106 a database is queried using the identification of the patient monitor received in step 104 to identify stored information regarding the spatial format of the display of physiological data on the patient monitor. The database that is queried may be local or remotely located to the computer so long as a sufficient data connection between the computer and the database exists.

Alternatively, and not depicted, the spatial format data may be received directly from the patient monitor while receiving the physiological data at step 102. The spatial format data may be received from the patient monitor rather than a receiving a signal identifying the patient monitor at step 104. The spatial format data may comprise coordinates that identify a spatial relationship for the physiological data within a display, as rather may identify the spatial relationship of physiological data values relative to each other.

Next, a signal indicative of the spatial format of the display of the physiological data on the patient monitor is received at step 108. The signal indicative of the spatial format may be received from the database. The signal received in step 108 is used to display the physiological data on the computer in the same spatial format as the display of the physiological data on the patient monitor at step 110. Finally, the display of the physiological data on the computer may be used to verify that the values of the physiological data displayed on the patient monitor match the values of the physiological data displayed on the computer.

Embodiments of the computer for use in the transfer and verification of data and the method of verifying the transfer of patient physiological data disclosed herein may present advantages over currently available devices and methods. Embodiments disclosed herein may provide the advantage of facilitating the verification of data that has been transferred by allowing a clinician to easily correlate the data displayed between the two devices. The improved visual correlation between the two devices provides the advantage of promoting efficiency in the verification process. Embodiments disclosed herein may improve both the speed of the verification process as well as reduce the likelihood that errors in the data presented on the two devices will go unnoticed. Specifically, the transposition of physiological parameter values may be more readily identifiable by a clinician verifying the transfer of the data using a device or method disclosed herein.

This written description uses examples to disclose features of the embodiments, including the best mode, and also to enable any person skilled in the art to make and use the invention. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Various alternatives and embodiments are contemplated as being with in the scope of the following claims, particularly pointing out and distinctly claiming the subject matter regarded as the invention.

What is claimed is:

1. An apparatus for use in the transfer and monitoring of data from a data recording device with a data recording device display that presents the data in a presentation format, the apparatus comprising:
   a computer display that presents data in a graphical user interface presented by the computer display;
   a controller connected to the computer display, wherein the controller operates to control the data presented by the computer display and the spatial arrangement of the data in the graphical user interface presented by the computer display;
   a first input device connected to the controller, the first input device receives data from the data recording device;
   a second input device connected to the controller, the second input device being operable to receive information identifying the data recording device;
   wherein the controller controls the computer display to present the data received from the data recording device and further controls the spatial arrangement of the data in the graphical user interface of the computer display based upon the received information identifying the data recording device which is used by the controller to identify the presentation format of the recording device display, wherein the controller controls the computer display to present the data received from the data recording device in a spatial arrangement according to the received information to mimic the appearance of a the presentation format of the data by the data recording device display.

2. The computer of claim 1, wherein the graphical user interface comprises a plurality of data regions, each data region being disposed to display data.

3. The computer of claim 2, wherein each data region is predetermined to display a predetermined data type and the appearance of the display of data by the data recording device display is mimicked by changing the arrangement of the data regions in the graphical user interface.

4. The computer of claim 1, wherein the data recording device is a patient physiological data monitor, and the data that is recorded by the data recording device and received by the first input device is patient physiological data.

5. The computer of claim 4, wherein the data recording device is a vital signs monitor, and the patient physiological data includes patient temperature, patient SpO2 and patient blood pressure.

6. The computer of claim 4, wherein the first input device comprises an electronic data transfer connection.

7. The computer of claim 4 wherein the second input device is a barcode scanner.

8. The computer of claim 4 wherein the second input device is a sensor for an receiving a signal from an RFID tag associated with the patient physiological data monitor.

9. The computer of claim 4 where the second input device receives a transmission of coordinate data from the data recording device.

10. A method of verifying the transfer of patient physiological data recorded by a patient monitor to a computer, the method comprising:
   acquiring patient physiological data with a patient monitor that includes a first graphical display;
   presenting the acquired patient physiological data on a graphical user interface (GUI) of the first graphical display in a first spatial format;
   receiving, with the computer, the acquired patient physiological data from the patient monitor;
   receiving, with the computer, a signal from the patient monitor, the signal being used to identify the first spatial format of the physiological data presented on the GUI of the first graphical display; and
   presenting the physiological data on a GUI of a second graphical display operated by the computer, wherein the physiological data is presented on the GUI of the second graphical display in the first spatial format.

11. The method of claim 10, further comprising:
   querying a database, with the computer, for stored information regarding the first spatial format of the display of the physiological data on the patient monitor using the signal from the patient monitor.

12. The method of claim 11 further comprising comparing physiological data displayed by the patient monitor to the physiological data displayed on the graphical display by the computer, to verify the transfer of the physiological data from the patient monitor to the computer.

13. The method of claim 12, further comprising scanning a bar code on the patient monitor to receive the signal indicative of the spatial format of the display of physiological data on the patient monitor.

14. The method of claim 12, further comprising receiving a signal from an RFID tag to receive the signal indicative of the spatial format of the display of physiological data on the patient monitor.

15. The method of claim 10 wherein the physiological data is received by the computer through manual entry of the data.

16. The method of claim 10, wherein the physiological data is received by the computer via an electronic transmission.

17. A system for transferring and verifying physiological data, the system comprising:
   a patient monitoring device comprising a first graphical display, the patient monitoring device obtains physiological data from a patient and presents the obtained physiological data in a graphical user interface (GUI) presented by the first graphical display, the obtained physiological data being presented in a first presentation format;
   a portable computer comprising a second graphical display, the portable computer receives the physiological data from the patient monitoring device, the portable computer further receives a signal indicative of the patient monitoring device and uses the signal to identify the first presentation format, wherein the portable computer controls the second graphical display to present the physiological data in the first presentation format in a GUI of the second graphical display; and
   a server communicatively connected to the portable computer, the server receives the physiological data from the portable computer and updates a stored electronic medical record (EMR) with the received physiological data.

18. The system of claim 17 wherein the portable computer transmits the physiological data to the server after the portable computer receives a verification that the physiological data presented by the first graphical display of the patient monitoring device matches the physiological data presented by the second graphical display of the portable computer.

19. The system of claim 18 wherein the portable computer receives the physiological data through manual entry.

* * * * *